United States Patent [19]
Kristiansen

[11] 3,948,921
[45] Apr. 6, 1976

[54] O-ETHYL-S-(PROPYL, BUTYL OR PROPARGYL)-S-[2,6-DICHLOROPICOLYL-(3)]-DITHIOPHOSPHATES

[75] Inventor: Odd Kristiansen, Reinach, Switzerland

[73] Assignee: Ciba-Geigy Corporation, Ardsley, N.Y.

[22] Filed: Nov. 5, 1974

[21] Appl. No.: 521,223

Related U.S. Application Data

[63] Continuation-in-part of Ser. No. 437,413, Jan. 28, 1974, abandoned.

[52] U.S. Cl............. 260/294.8K; 424/263; 424/200
[51] Int. Cl.²........................................ C07D 213/65
[58] Field of Search................. 260/294.8 K, 297 P; 424/263

[56] References Cited
UNITED STATES PATENTS 3,371,095  2/1968  Lorenz et al................. 260/294.8 K
3,743,648  7/1973  Rigterink ..................... 260/294.8 K Primary Examiner—Alan L. Rotman
Attorney, Agent, or Firm—Frederick H. Rabin

[57] ABSTRACT

Picolyldithiophosphoric acid esters of the formula

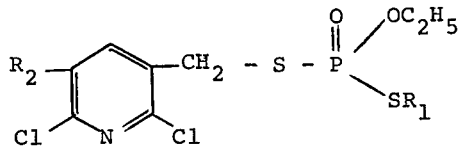

wherein $R_1$ represents n-propyl, isopropyl, sec.butyl or propargyl and $R_2$ represents hydrogen or chlorine, their manufacture and their use in pest control.

4 Claims, No Drawings

O-ETHYL-S-(PROPYL, BUTYL OR PROPARGYL)-S-[2,6-DICHLOROPICOLYL-(3)]-DITHIOPHOSPHATES

CROSS REFERENCE TO RELATED APPLICATIONS.

This is a continuation-in-part of application Ser. No. 437,413 filed Jan. 28, 1974, now abandoned.

The present invention relates to picolyldithiophosphoric acid esters, to a process for their manufacture and to their use in pest control.

The picolyldithiophosphoric acid esters have the formula

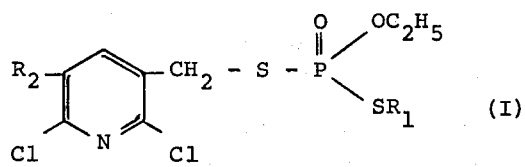

wherein $R_1$ represents n-propyl, isopropyl, sec.butyl or propargyl and $R_2$ represents hydrogen or chlorine.

Preferred compounds on account of their action are those of the formula I, wherein $R_1$ represents n-propyl or isopropyl and $R_2$ represents hydrogen.

The compounds of the formula I can be manufactured by methods which are analogous to known ones, e.g. in the following manner:

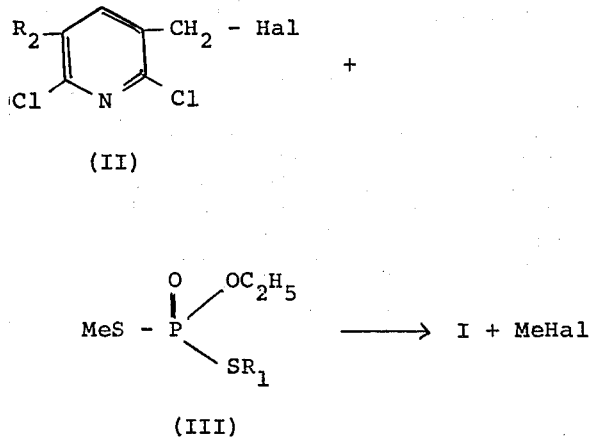

wherein $R_1$ and $R_2$ have the meanings given for the formula I and Hal represents a halogen atom, e.g. fluorine, chlorine, bromine or iodine, in particular chlorine or bromine, and Me represents an alkali metal, especially sodium or potassium.

The process is carried out at normal pressure, at a temperature between 0° to 150°, preferably between 20° to 100° C, and in solvents or diluents which are inert towards the reactants. Examples of suitable solvents and diluents are: aromatic hydrocarbons, e.g. benzene, toluene, halogenated hydrocarbons, chlorobenzene, polychlorobenzenes, bromobenzene, chlorinated alkanes with 1 to 3 carbon atoms, ethers, e.g. dioxan, tetrahydrofuran; esters, e.g. ethyl acetate; ketones, e.g. acetone, methyl ethyl ketone, diethyl ketone; nitriles, e.g. acetronitrile, etc.

Some of the starting materials of the formula II are known or can be manufactured by methods analogous to known ones.

The compounds of the formula I exhibit a broad biocidal activity and can be used for the contorl of a variety of plant and animal pests.

Compared with analogous compounds from U.S. Pat. No. 3,304,226 and U.S. Pat. No. 3,371,095, compounds of formula I have a surprisingly better insecticidal action, particularly against insects such as *Spodoptera littoralis* and *Heliothis virescens*.

The action of the compounds according to the invention extends, in addition, to all development stages, such as, e.g. eggs, larvae, nymphs, pupae and adults of insects of the families: Acrididae, Blattidae, Gryllidae, Gryllotalpidae, Tettigoniidae, Cimicidae, Phyrrhocoridae, Reduviidae, Aphididae, Delphacidae, Diaspididae, Pseudococcidae, Chrysomelisae, Coccinellidae, Bruchidae, Scarabaeidae, Dermestidae, Tenebrionidae, Curculionidae, Tineidae, Noctuidae, Lymantriidae, Pyralidae, Galleridae, Culicidae, Tipulidae, Stomoxydae, Muscidae, Calliphoridae, Trypetidae, Pulicidae as well as Acaridae of the families: Ixodidae, Argasidae, Tetranychidae Dermanyssidae.

By addition of other indecticides and/or acaricides it is possible to improve substantially the insecticidal or acaricidal action and to adapt it to given circumstances.

Examples of suitable additives are: organic phosphorus compounds, nitrophenols and derivatives thereof; formamidines; ureas; carbamates and chlorinated hydrocarbons.

In addition to the above mentioned properties, the compounds of the formula I also exhibit a microbiocidal action. Thus a number of these compounds display bactericidal action. But they are active chiefly against fungi, especially against phytopathogenic fungi belonging to the following classes: Oomycetes, Zygomycetes, Ascomycetes, Basidiomycetes, Denteromycetes.

The compounds of the formula 1 also exhibit a fungitoxic action against fungi which attack the plants from the soil. The new active substances are also suitable for treating seeds, fruit, tubers etc. from attack by fungus infections. The compounds of the formula I are also suitable for combating phytopathogenic nematodes.

The compounds of the formula I may be used as pure active substance of together with suitable carriers and/or additives. Suitable carriers and additives can be solid or liquid and correspond to the substances conventionally used in formulation technology, for example natural or regenerated substances, solvents, dispersants, wetting agents, adhesives, thickeners, binders and/or fertilisers.

For application, the compounds of the formula I may be processed to dusts, emulsion concentrates, granules, dispersions, sprays, to solutions or suspensions, in the conventional formulation which is commonly employed in application technology. Mention is also to be made of cattle dips and spray races, in which aqueous preparations are used.

The agents according to the invention are manufactured in known manner by intimately mixing and/or grinding active substances of the formula I with the suitable carriers, optionally with the addition of dispersants or solvents which are inert towards the active substances. The active substances can take, and be used in, the following forms: Solid forms:

dusts, tracking agents, granules, coated granules, impregnated granules and homogeneous granules.

Liquid forms:
a. active substances which are dispersible in water: wettable powders, pasts, emulsions:
b. solutions.

The content of active substance in the above described agents is between 0.1 to 95%, in which connection it should be mentioned that, in the case of application from aircraft or some other suitable means of application, it is possible to use concentrations of up to 99.5% or even pure active substance.

The active substances of the formula I can, for example, be formulated as follows:

Dusts

The following substances are used to manufacture (a) a 5% and (b) a 2% dust:
a. 5 parts of active substance
   95 parts of talcum
b. 2 parts of active substance
   1 part of highly disperse silicic acid
   97 parts of talcum.

The active substances are mixed with the carriers and ground.

Granules

The following substances are used to produce 5% granules:
   5 parts of active substance,
   0.25 parts of epichlorohydrin,
   0.25 parts of cetyl polyglycol ether,
   3.50 parts of polyethylene glycol,
   91 parts of kaolin (particle size 0.3–0.8 mm).

The active substance is mixed with epichlorohydrin and dissolved with 6 parts of acetone; the polyethylene glycol and cetyl polyglycol ether are then added. The resulting solution is sprayed on kaolin, and the acetone is subsequently evaporated in vacuo.

Wettable powder:

The following constituents are used for the preparation of (a) a 40%, (b) and (c) a 25%, and (d) a 10% wettable powder:
a. 40 parts of active substance,
   5 parts of sodium lignin sulphonate,
   1 part of sodium dibutyl-naphthalene sulphonate,
   54 parts of silicic acid.
b. 25 parts of active substance
   4.5 parts of calcium lignin sulphonate,
   1.9 parts of Champagne chalk/hydroxyethyl cellulose mixture (1:1),
   1.5 parts of sodium dibutyl naphthalene sulphonate,
   19.5 parts of silicic acid,
   19.5 parts of Champagne chalk,
   28.1 parts of kaolin.
c. 25 parts of active substance,
   2.5 parts of isooctylphenoxy-polyoxyethylene-ethanol,
   1.7 parts of Champagne chalk/hydroxyethyl cellulose mixture (1:1),
   8.3 parts of sodium aluminium silicate,
   16.6 parts of kieselguhr,
   46 parts of kaolin.
d. 10 parts of active substance,
   3 parts of a mixture of the sodium salts of saturated fatty alcohol sulphates,
   5 parts of naphthalenesulphonic acid/formaldehyde condensate,
   82 parts of kaolin.

The active substances are intimately mixed, in suitable mixers, with the additives, the mixture being then ground in the appropriate mills and rollers. Wettable powders are obtained which can be diluted with water to give suspensions of any desired concentration.

Emulsifiable concentrates:

The following substances are used to produce (a) a 10% and (b) a 25% emulsifiable concentrate:
a. 10 parts of active substance,
   3.4 parts of epoxidised vegetable oil,
   3.4 parts of a combination emulsifier consisting of fatty alcohol polyglycol ether and alkylaryl sulphonate calcium salt,
   40 parts of dimethylformamide,
   43.2 parts of xylene,
   25 parts of active substance,
   2.5 parts of epoxidised vegetable oil,
   10 parts of an alkylarylsulphonate/fatty alcohol-glycol ether mixture,
   5 parts of dimethylformamide,
   57.5 parts of xylene.

From these concentrates it is possible to produce, by dilution with water, emulsions of any desired concentration.

Spray:

The following constituents are used to prepared a 5% spray:
   5 parts of active substance,
   1 part of epichlorohydrin,
   94 parts of benzene (boiling limits 160°–190°C).

EXAMPLE 1

Manufacture of
O-ethyl-S-n-propyl-S-2,6-dichloropicolyl-3-phosphoric thiolate

14 G of 2,6-dichloropicolyl-3-chloride are dissolved in 150 ml of acetone, and to this solution are added by small amounts 16.9 g of potassium-O-ethyl-S-n-propyl-dithiophosphate. The reaction mixture is stirred for 16 hours at room temperature. After the solvent has been distilled off, the residue is treated with ether, washed with water, and dried over anhydrous sodium sulphate.

The ether is evaporated off to yield the compound of the formula

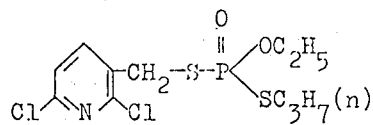

with a refractive index of $n_D^{24} = 1.5740$.

The following compounds are also manufactured in analogous manner:

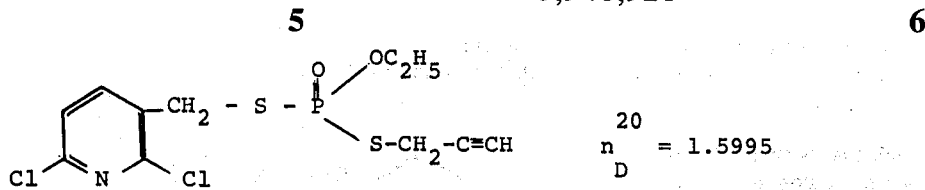

$n_D^{20} = 1.5995$

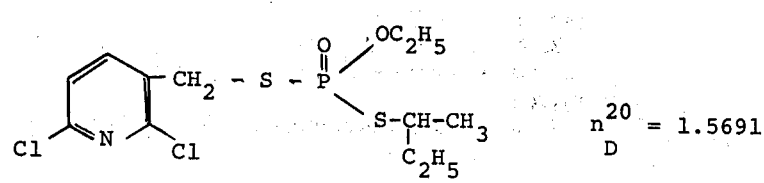

$n_D^{20} = 1.5691$

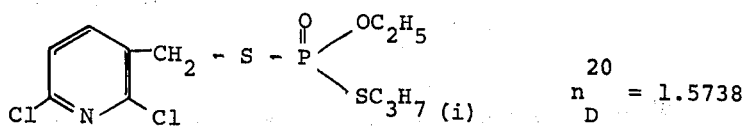

$n_D^{20} = 1.5738$

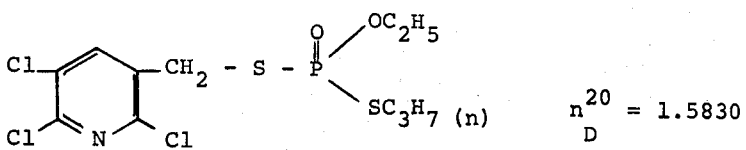

$n_D^{20} = 1.5830$

EXAMPLE 2

A. Insecticidal ingest poison action

Cotton and potato plants were sprayed with a 0.05% aqueous emulsion (obtained from a 10% emulsifiable concentrate). After the coating had dried, the cotton plants were populated with *Spodoptera littoralis* or *Heliothis virescens* larvae $L_3$ and the potato plants with Colorado potato bettle larvae (*Leptinotarsa decemlineata*). The test was carried out at 24°C and 60% relative humidity. In the above test, the compounds according to Example 1 displayed good ingest poison action against *Spodoptera littoralis*. *Heliothis* and *Leptinotarsa decemlineata* larvae.

B. Systemic insecticidal action

To determine the systemic action, rooted bean plants (*Vicia fabae*) were put into a 0.01% aqueous active substance solution (obtained from a 10% emulsifiable concentrate). After 24 hours, aphide (*Aphis fabae*) were placed on the parts of the plant above the soil. The aphids were protected from contact and gas action by means of a special device. The test was carried out at 24° and 70°C relative humidity. In the above test, the compounds according to Example 1 have systemic action against *Aphis fabae*.

EXAMPLE 3

Action against *Chilo suppressalis*

Six rice plants at a time of the variety Caloro were transplanted into plastic pots (diameter at the top = 17 cm) and reared to a height of about 60 cm. Infestation with *Chilo suppressalis* larvae ($L_1$: 3–4 mm long) took place 2 days after the active substance had been applied in granule form to the paddy water (rate of application: 8 kg of active substance per hectare). Evaluation of the insecticidal action took place 10 days after application of the granules. The compounds according to Example 1 were active in the above test against *Chilo suppressalis*.

EXAMPLE 4

Action against ticks

A. *Rhipicephalus bursa*

Five adult ticks and 50 tick larvae were counted into a glass tube and immersed for 1 to 2 minutes in 2 ml of an aqueous emulsion from an emulsion series each containing 100, 10, 1 or 0.1 ppm of test substance. The tube was then sealed with a standard cotton wool plug and placed on its head, so that the active substance emulsion could be absorbed by the cotton wool.

In the case of the adults evaluation took place after 2 weeks, and in that of the larvae after 2 days. Each test was repeated twice.

B. *Boophilus microplus* (larvae)

Tests were carried out in each case with 20 OP-sensitive larvae using a dilution series analogous to that of test A. (The resistance refers to the tolerability of Diazinon). The compounds according to Example 1 acted in these tests against adults and larvae of *Rhipicephalus bursa* and sensitive and OP-resistant larvae of *Boophilus microplus*.

EXAMPLE 5

Acaricidal action

*Phaseolus vulgaris* (dwarf beans) have an infested piece of leaf from a mass culture of *Tetranychus urticae* placed on them 12 hours before the test for the acaricidal action. The mobile stages which have invaded the plants are sprayed with the emulsified test preparations from a chromatography atomiser so that the spray broth does not run off. The number of living and dead larvae, adults and eggs are evaluated after 2 to 7 days under a stereoscopic microscope and the result expressed in percentages. During the "waiting time", the treated plants are kept in greenhouse compartments at 25°C. The compounds according to Example 1 were active in the above test against eggs, larvae and adults of *Tetranychus urticae*.

EXAMPLE 6

Action against soil nematodes

To the test against soil nematodes, the active substance in the respective concentration is applied to and intimately mixed with soil infected with root gall nematodes (*Meloidgyne arenaria*). Immediately afterwards, tomato cuttings are planted in the prepared soil in a series of tests and after a waiting time of 8 days tomato seeds are sown in another test series. In order to assess the nematocidal action, the galls present on the roots are counted 28 days after planting and sowing respectively. In this test the compounds according to Example 1 display good action against *Meloidgyne arenaria*.

We claim:

1. A compound of the formula

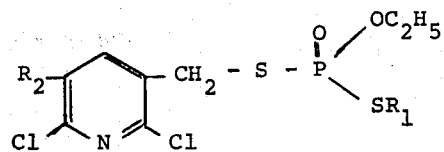

wherein $R_1$ represents n-propyl, isopropyl, sec.butyl or propargyl, and $R_2$ represents hydrogen or chlorine.

2. A compound according to claim 1, wherein $R_1$ represents n-propyl or isopropyl, and $R_2$ represents hydrogen.

3. The compound according to claim 2 of the formula

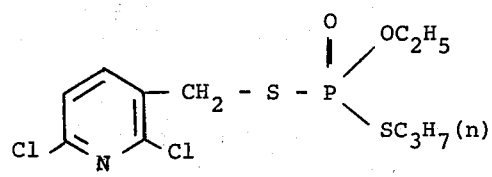

4. The compound according to claim 2 of the formula

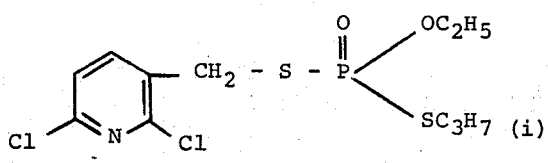

* * * * *

UNITED STATES PATENT OFFICE
CERTIFICATE OF CORRECTION

Patent No. 3,948,921  Dated April 6, 1976

Inventor(s) Odd Kristiansen

It is certified that error appears in the above-identified patent and that said Letters Patent are hereby corrected as shown below:

The following should be inserted in the Heading:

FOREIGN APPLICATION PRIORITY DATA

February 7, 1973   Switzerland .......1756/73

December 20, 1973  Switzerland .......17774/73

Signed and Sealed this twenty-ninth Day of June 1976

[SEAL]

Attest:

RUTH C. MASON
Attesting Officer

C. MARSHALL DANN
Commissioner of Patents and Trademarks